(12) United States Patent
Castagneto et al.

(10) Patent No.: US 11,179,257 B2
(45) Date of Patent: Nov. 23, 2021

(54) EXPANDABLE INTRAGASTRIC DEVICE

(71) Applicant: KEYRON LTD, London (GB)

(72) Inventors: Marco Castagneto, Rome (IT);
Giorgio Castagneto Gissey, Rome (IT)

(73) Assignee: KEYRON LTD, London (GB)

(*) Notice: Subject to any disclaimer, the term of this patent is extended or adjusted under 35 U.S.C. 154(b) by 137 days.

(21) Appl. No.: 16/316,757

(22) PCT Filed: Sep. 1, 2017

(86) PCT No.: PCT/IB2017/055259
§ 371 (c)(1),
(2) Date: Jan. 10, 2019

(87) PCT Pub. No.: WO2018/060788
PCT Pub. Date: Apr. 5, 2018

(65) Prior Publication Data
US 2019/0314180 A1 Oct. 17, 2019

(30) Foreign Application Priority Data

Sep. 28, 2016 (IT) .................. 102016000097363

(51) Int. Cl.
*A61F 5/00* (2006.01)
(52) U.S. Cl.
CPC ............ *A61F 5/003* (2013.01); *A61F 5/0076* (2013.01); *A61F 5/0036* (2013.01); *A61M 2210/1053* (2013.01)
(58) Field of Classification Search
CPC combination set(s) only.
See application file for complete search history.

(56) References Cited

U.S. PATENT DOCUMENTS

| 2005/0228504 A1 | 10/2005 | Demarais |
| 2012/0095483 A1 | 4/2012 | Babkes |
| 2016/0095731 A1 | 4/2016 | Connor |

FOREIGN PATENT DOCUMENTS

| WO | 2012054413 A2 | 4/2012 | |
| WO | WO-2015085010 A1 * | 6/2015 | ......... A61F 5/0036 |

OTHER PUBLICATIONS

International Search Report and Written Opinion for Corresponding International Application No. PCT/IB2017/055259 (14 Pages) (dated Nov. 27, 2017).

* cited by examiner

*Primary Examiner* — Anh T Dang
(74) *Attorney, Agent, or Firm* — Lucas & Mercanti, LLP

(57) ABSTRACT

An expandable intragastric device, configured for being positioned into the stomach by an endoscopic procedure is provided. The device is capable of assuming a minimum-encumbrance configuration for delivery into the stomach and an expanded configuration for use in situ. The device also includes a balloon structure, which is capable of assuming a deflated configuration for delivery into the stomach and an inflated configuration for occupying a part of the stomach inner space. The overall configuration of the device is such that, once it is delivered in the stomach, food passes into the inner lumen of the supporting tubular body and into the intestine.

11 Claims, 2 Drawing Sheets

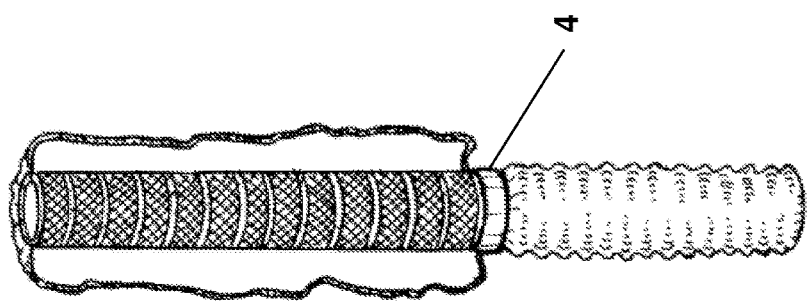
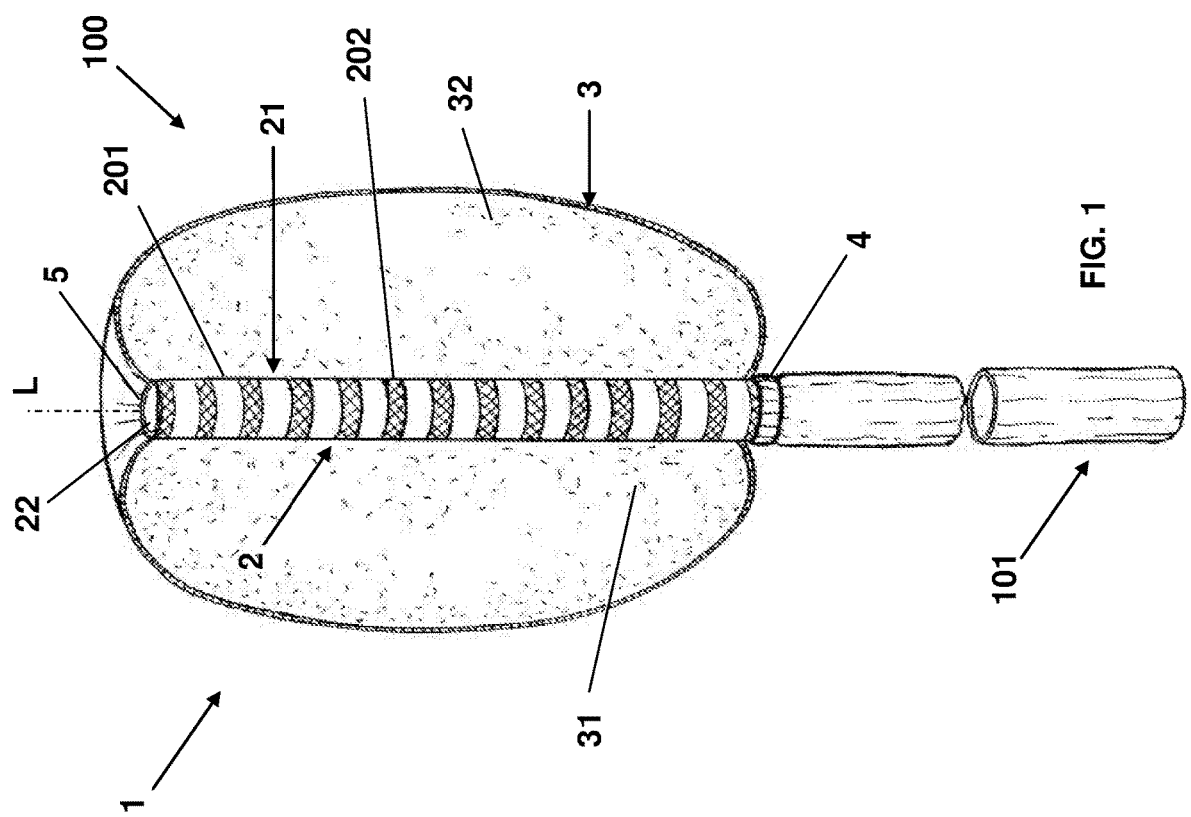

EXPANDABLE INTRAGASTRIC DEVICE

CROSS-REFERENCE TO RELATED APPLICATIONS

This application is a 371 of PCT/IB2017/055259, filed Sep. 1, 2017, which claims the benefit of Italian Patent Application No. 102016000097363, filed Sep. 28, 2016.

FIELD OF THE INVENTION

The present invention relates to an expandable device suitable to be implanted in the stomach through an endoscopic procedure.

The device belongs mainly to the category of products conceived for the treatment of obesity and related diseases.

BACKGROUND OF THE INVENTION

The prevalence of overweight and obesity is monitored worldwide by the World Health Organization (WHO). Obesity prevalence has doubled since 1980, i.e. in less than forty years.

Both overweight and obesity result from the imbalance between energy intake and energy expenditure, occurring in individuals with high food intake, in particular of high density food, and lower levels of physical activity.

Obesity represents an independent risk factor of death and appears to reduce life expectancy.

Overweight and obesity are also major predictors of "type 2" diabetes (T2D) incidence.

Furthermore, obesity is associated with a myriad of other complications, including hypertension, arthritis, coronary heart disease, stroke, sleep apnea, polycystic ovary syndrome and a large number of additional major diseases.

The compliance to lifestyle modifications appears, generally speaking, poor.

Bariatric surgery—in particular gastric bypass, sleeve gastrectomy, adjustable gastric band, and biliopancreatic diversion with or without duodenal switch—is associated with a much larger and durable weight loss, but also with mortality and high rates of complication and reoperation. However, bariatric surgery shows a large positive effect in improving glycaemic control up to the remission of diabetes.

Due to said association with mortality and complications, however, bariatric surgery should be considered only as a secondary option in the treatment of obesity. To this end, a series of new and less invasive strategies have been developed.

Intragastric balloon was conceived with the intention of increasing gastric content and reducing appetite.

WO2012/054413A2 discloses a space-filling intragastric implant device which reacts within the stomach to induce satiety.

However, recent reviews of the literature have demonstrated that intragastric balloon does not show convincing evidence of a greater and durable weight loss compared with conventional management. Moreover, the balloon can migrate and determine intestinal occlusion.

The so-called "endobarrier gastrointestinal liner", or duodenal-jejunal bypass sleeve (DJBS), was introduced to supposedly improve glycaemic control in T2D. However, while it is effective in inducing weight loss, recent literature failed to find a significant effect on diabetes. In addition, it appears associated with relevant complications such as hepatic abscess, gastro-intestinal bleeding, abdominal pain, nausea and vomiting.

Therefore, the state of the art reveals a need for new, safe and minimally invasive devices that are able to reduce weight loss in obese subjects.

SUMMARY OF THE INVENTION

The technical problem underlying the present invention is therefore to provide a device which satisfies the needs and overcomes the drawbacks mentioned above with reference to the state of the art.

The above problem is solved by a device according to claim 1.

Preferred features of the invention are object of the dependent claims.

In the present disclosure, the terms "distal" and "proximal", or derivatives thereof, are used to denote greater or lower proximity to the upper or lower end of the gastro-intestinal tract.

The device of the invention overcomes or ameliorates the problems associated with weight loss surgery, or reduces the likelihood of the related complications, repercussions, side effects and malfunctions.

The device comprises an inflatable gastric balloon that is built around an expandable gastric tube, the latter preferably with a stent-like construction.

The distal end of the expandable gastric tube is configured to be positioned immediately below the pylorus, i.e. distal to the stomach.

According to a most preferred embodiment, the expandable gastric tube can be attached to a flexible intestinal tube, made of a non-permeable or semi-permeable material, which reaches the proximal jejunum.

The device can be made of flexible material(s).

The device can be made in variable sizes.

The device is positioned in a deflated state into the stomach, preferably by means of an endoscope. Once delivered in situ, the gastric balloon is filled with any suitable and well-tolerated solution, fluid and/or gas. Inflation of the balloon can also make the gastric tube expand longitudinally, or in any other direction.

In order to conform to the shape of the stomach, the balloon is preferably restricted below and enlarged above. Its action regarding the residual stomach size can, therefore, mimic a gastric bypass or a partial gastrectomy.

In a preferred embodiment, the balloon is capable of reducing the gastric volume by any percentage, preferably at least 60%, so the food can pass through the gastric tube that is located inside the balloon. Food can thus be delivered directly into the duodenum or pass through the intestinal tube, and thereafter into the jejunum. Hence, the device can mimic a restrictive bariatric operation or a restrictive and malabsorptive bariatric operation.

In order to reduce the possibility of ulceration of the gastric mucosa, the exterior of the balloon can may be made of an uneven surface; thus, the gastric peristalsis will permit to change continuously the contact points between the balloon wall and the gastric mucosa.

Other advantages, features and use modes of the present invention will result evident from the following detailed description of some embodiments, provided by way of example and not with limitative purpose.

BRIEF DESCRIPTION OF THE DRAWINGS

Reference will be made to the figures of the annexed drawings, wherein:

FIG. 1 shows a frontal perspective view of an apparatus and device according to a preferred embodiment of the present invention, in an expanded configuration;

FIG. 2 shows an enlarged, frontal perspective view of the device of FIG. 1 in a deflated, or minimal-encumbrance, configuration.

DETAILED DESCRIPTION OF PREFERRED EMBODIMENTS OF THE INVENTION

Figure 3:
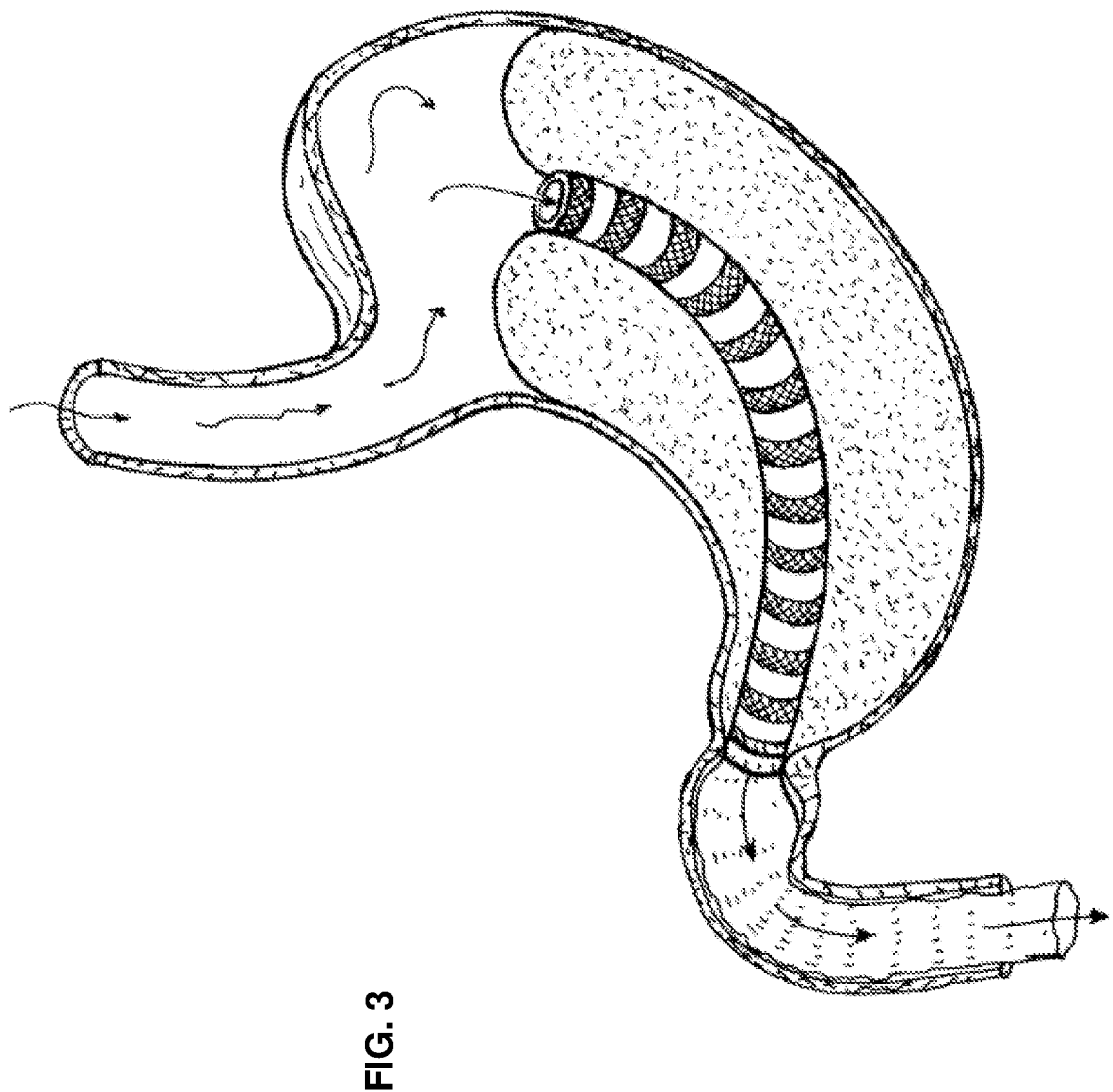
FIG. 3 shows a perspective view of the device of FIG. 1 implanted in the stomach of a patient, in a fully expanded, or deployed, configuration.

An expandable intragastric device (henceforth, 'device 1'), according to a preferred embodiment of the invention, is shown in FIGS. 1 to 3.

In the present embodiment, device 1 is an integral part of an implantable apparatus 100, the latter including also a gastrointestinal liner 101, in particular a duodenal-jejunal bypass sleeve. The latter is preferably of variable length.

Variant embodiments provide that the device of the invention is connectable to said duodenal-jejunal bypass sleeve as a separate and/or independent component.

In other embodiments, the device of the invention can be used without said variable length duodenal-jejunal bypass sleeve or any other tubular structure configured to be implanted in the proximal and/or distal intestine.

Device 1 is configured for being positioned into the stomach by an endoscopic procedure, or any other procedure.

Device 1 comprises a support tubular body 2 having an oblong shape along a preferably longitudinal extension L. In particular, supporting tubular body 2 comprises a sidewall skirt 21 defining an inner through lumen 22. The latter is configured for allowing a food flow therethrough.

Support tubular body 2 is made of a main carrier structure 201, preferably made of an expandable material, for example elastic or semi-elastic, along said extension L. Carrier structure 201 supports a plurality of stent-like, or mesh-like, elements 202. Alternatively, the whole or a continuous part of body 2 can be made entirely of such stent-like, or mesh-like, elements.

Due to said configuration/construction, supporting tubular body 2 is expandable along said longitudinal extension L so as to being capable of assuming a minimum-encumbrance configuration (FIG. 2) for delivery into the stomach and an expanded configuration (FIGS. 1 and 3) for use in situ.

Preferably, supporting tubular body 2 has an expanded length along said longitudinal extension L comprised in a range of 15-30 cm.

Preferably, supporting tubular body 2 has, at a distal end portion thereof, a terminal ring 4, which, in use, is positioned below the pylorus in order to keep device 1 into a stable position.

As said above, tubular body 2 is connected or connectable to sleeve 101, or to another tubular structure, at its distal end portion. Sleeve 101, or an alternative tubular structure, is preferably made of pliable and soft material of varying length and of different permeability properties.

Device 1 comprises also a balloon structure 3, connected to sidewall skirt 21 of supporting tubular body 2 and made of an elastic, semi-elastic or anyhow expandable material or construction.

In the present embodiment, balloon structure 3 comprises two chambers, denoted by 31 and 32 respectively, in fluid communication therebetween.

Alternatively, balloon structure 3 can be configured as a double inflatable chamber tube or even as a single chamber.

In alternative configurations, the gastric balloon can include thereinside one or more inner balloons.

Additional balloons external or internal to one or more main balloons can also be provided, also in order to prevent device migration into the intestine and/or to reduce device movements inside the stomach.

Balloon structure 3, and particularly each of its chambers 31 and 32, is capable of assuming a deflated configuration for delivery into the stomach (FIG. 2) and an inflated configuration for occupying a part of the stomach inner space (FIGS. 1 and 3).

Therefore, the overall configuration of device 1 is such that, once it is delivered in the stomach, food passes into inner lumen 22 of supporting tubular body 2 and into the intestine.

In a preferred embodiment, balloon structure 3 has a self-sealing valve 5 arranged proximally, which allows a selective injection of one or more fluids and/or gas for filling balloon structure 3 to the appropriate size. Filling of the two chambers 31 and 32 can be achieved jointly or independently.

As shown in FIG. 3, in order to conform to the shape of the stomach, in a preferred embodiment balloon structure 3, and/or one or each of its chambers 31 and 32, is shaped in a substantially tapered fashion, being restricted below (distally) and enlarged above (proximally).

Preferably, balloon structure 3 has an uneven, or irregular, external surface contacting the stomach, so that, in use, gastric peristalsis determines a change of the points of contact with the stomach tissue.

The entire device, or part of it, can be made of biocompatible, elastic, or biodegradable materials. In particular, main carrier structure 201 of supporting tubular body 2 can be made of a material selected in a group comprising: nickel, titanium, nitinol, elgiloy, PEEK, PEAK, PEK, PEKK, PEKKEK, plastic or any radio opaque fibre, or a combination of the aforementioned materials, or any other suitable material.

Balloon structure 3 can be made of a material selected in a group comprising: silicone, polydiphenylsilaxane (PDPS), polythmethylsiloxane (PDMS), a combination of the aforementioned materials, or any other suitable material.

The sleeve is made of fluropolymers, Polyurethane, or any other suitable material, with a radio opaque terminal.

In use, the device is positioned in a deflated state into the stomach, preferably via an endoscope. Once delivered in situ, the gastric balloon is filled with any suitable and well-tolerated solution, fluid, and/or gas, for instance saline added with traces of methylene blue, or another vital colour, or with foam. In the present embodiment, inflation of balloon structure 3 determines the expansion, preferably a longitudinal expansion, of supporting tubular body 2, too.

In its shortest form, the device can have a height up to 5 cm in its gastric part, it can be used to take in place the duodenal-jejunal sleeve.

Given the setup of device 1, it helps reducing food intake and obtain weight loss better than a simple intragastric balloon, in addition to providing reduction in plasma glucose and insulin levels.

During permanence of device 1 in the gastro-intestinal tract, the patient may be followed with a motivation program to change eating habits following a diet and a program of behavioural modification.

The device can be used also to treat gastric strictures.

In particular, in case of stenosis of the pylorus the prior art uses stents, which however tend to migrate and may determine intestinal occlusions. In this application, the use of a gastric balloon of appropriate size as those described above may allow avoiding such migration. Similar considerations apply for gastric post-surgical stenosis.

The present invention has been described so far with reference to preferred embodiments. It is intended that there may be other embodiments which refer to the same inventive concept, that may fall within the scope of the appended claims.

The invention claimed is:

1. An expandable intragastric device, configured for being positioned into a stomach in an endoscopic procedure, which device comprises:
   a supporting tubular body having an oblong shape along a longitudinal extension, said supporting tubular body comprising a sidewall skirt defining an inner through lumen, wherein said supporting tubular body is expandable along said longitudinal extension thereby convertible between a minimum-encumbrance configuration for delivery into the stomach and an expanded configuration with an increased length for use in situ; and
   a balloon structure, connected to said sidewall skirt of said supporting tubular body thereby covering a portion of said supporting tubular body, which balloon structure is convertible between a deflated configuration for delivery into the stomach and an inflated configuration for occupying a part of stomach inner space,
   wherein the overall configuration of the device allows food to pass into said inner through lumen of said supporting tubular body and into intestine after the device is positioned in the stomach, and
   wherein said covered portion of said supporting tubular body has a constant outer diameter both in the deflated configuration of said balloon structure and in the inflated configuration of said balloon structure.

2. The device according to claim 1, wherein said sidewall skirt of said supporting tubular body comprises a stent-like, or mesh-like, construction.

3. The device according to claim 1, wherein an exterior of said balloon structure has is made of an uneven, or irregular, external surface whereby gastric peristalsis determines a change of points of contact with stomach tissue.

4. The device according to claim 1, wherein said supporting tubular body has an increased length along said longitudinal extension in a range of about 15-30 cm.

5. The device according to claim 1, wherein said supporting tubular body has a main carrier structure made of a material selected from the group consisting of: nickel, titanium, nitinol, elgiloy, fluropolymers, PEEK, PEAK, PEK, PEKK, PEKKEK, plastic, a radio opaque fibre, and combinations of the aforementioned materials.

6. The device according to claim 1, wherein said balloon structure is made of a material selected from the group consisting of: silicone, polydiphenylsiloxane (PDPS), polydimethylsiloxane (PDMS), and combinations of the aforementioned materials.

7. The device according to claim 1, wherein said supporting tubular body has opposing ends and said balloon structure is connected to said sidewall skirt of said supporting tubular body at said opposing ends.

8. An implantable apparatus, including an expandable intragastric device according to claim 1 and a gastrointestinal liner, connected or connectable with said supporting tubular body at a distal end portion of such supporting tubular body.

9. The apparatus according to claim 8, wherein said gastrointestinal liner is made of fluoropolymers.

10. The apparatus according to claim 9, wherein said gastrointestinal liner comprises a radio opaque terminal.

11. The apparatus according to claim 8, wherein said gastrointestinal liner is a duodenal-jejunal bypass sleeve.

\* \* \* \* \*